United States Patent [19]

Yamaguchi et al.

[11] Patent Number: 5,712,167
[45] Date of Patent: Jan. 27, 1998

[54] METHOD OF MEASURING AMADORI COMPOUND BY LIGHT SCATTERING

[75] Inventors: Yoshinori Yamaguchi; Xiaoming Dou; Masayuki Yagi; Harumi Uenoyama, all of Kyoto, Japan

[73] Assignee: Kyoto Dai-Ichi Kagaku Co., Ltd., Kyoto, Japan

[21] Appl. No.: 682,219

[22] Filed: Jul. 17, 1996

[30] Foreign Application Priority Data

Jul. 19, 1995 [JP] Japan ................................ 7-206559

[51] Int. Cl.$^6$ ........................................... G01N 21/47
[52] U.S. Cl. ............................ 436/87; 436/111; 436/171
[58] Field of Search ................................ 436/86, 87, 88, 436/92–95, 164, 171, 111

[56] References Cited

U.S. PATENT DOCUMENTS

| | | | |
|---|---|---|---|
| 5,284,777 | 2/1994 | Rosenthal et al. | 436/88 |
| 5,312,759 | 5/1994 | Hama et al. | 436/88 |
| 5,370,990 | 12/1994 | Staniford et al. | 436/88 |
| 5,372,997 | 12/1994 | Inoue et al. | 436/88 |
| 5,565,170 | 10/1996 | Sakamoto | 436/87 |

OTHER PUBLICATIONS

Chira, I.S. et al. "Light Scattering by Blood Components after Supplying Glucose" Chemical Abstracts, vol. 114, No. 19, Abstract No. 181535u (1991).

*Primary Examiner*—Jeffrey Snay
*Attorney, Agent, or Firm*—Nikaido Marmelstein Murray & Oram LLP

[57] ABSTRACT

In order to quantitatively measure an Amadori compound by a simple optical method utilizing light scattering, a sample containing an Amadori compound which is stored in a cell is irradiated with excitation light from an He—Ne laser unit so that scattered light from the sample is received and separated into its spectral components for obtaining a light scattering spectrum, and a light scattering peak existing at 820 to 840 $cm^{-1}$, 1655 to 1660 $cm^{-1}$, 2000 to 2020 $cm^{-1}$, 2080 to 2100 $cm^{-1}$, 2460 to 2470 $cm^{-1}$ or 2530 to 2600 $cm^{-1}$ in shift wavenumber with respect to the excitation wavelength in the light scattering spectrum is detected by a detector. The saccharide concentration or the saccharification ratio of the Amadori compound is measured by a calibration curve through the peak intensity or the peak integral value of the light scattering peak.

7 Claims, 13 Drawing Sheets

METHOD OF MEASURING AMADORI COMPOUND BY LIGHT SCATTERING

BACKGROUND OF THE INVENTION

1. Field of the Invention

The present invention relates to a method of making quantitative measurement of an Amadori compound such as saccharified albumin, saccharified hemoglobin or saccharified globulin.

2. Description of the Background Art

When a substance (hereinafter referred to as protein or the like) having an amino group such as protein, peptide or amino acid coexists with reducing sugar such as aldose, partial amino and aldehyde groups are nonenzymatically and non-reciprocally bonded to each other to cause Amadori rearrangement, thereby forming an Amadori compound. The formation rate of the Amadori compound is expressed in a function such as the concentration of the reactive substance, the contact time, the temperature or the like. Thus, it is considered that various data related to the substance containing the reactive substance can be obtained from the amount of formation thereof. Substances containing Amadori compounds are food such as soy sauce, body fluids such as blood and the like.

In an organism, for example, glucose is bonded to amine acid, to form a fructosylamine derivative which is an Amadori compound. A fructosylamine derivative formed by saccharification of hemoglobin in the blood is called glycohemoglobin, a fructosylamine derivative formed by saccharification of albumin is called glycoalbumin, and a fructosylamine derivative formed by saccharification of protein in the blood is called fructosamine. The intravascular concentration of such a fructosylamine derivative reflects the average blood-sugar level in a past constant period and its measured value can be an important index for diagnosis of a diabetic condition and control of the condition, and hence establishment of Amadori compound measuring means is clinically extremely useful. Further, it is possible to recognize the state and the period of preservation of food after production by determining an Amadori compound contained in the food, and this is conceivably usefully for quality control.

Thus, quantitative analysis of an Amadori compound is useful over wide fields including those of medical science and food.

In general, a method utilizing high-speed liquid chromatography (refer to Chromatogr. Sci., 10, 659 (1979)), a method employing a column which is filled with a solid bonded to boric acid (refer to Clin. Chem., 28, 2088 (1982) electrophoresis (refer to Clin. Chem. 16, 1598 (1980)), a method utilizing antigen-antibody reaction (refer to JJCLA, 18, 620 (1993) and Kiki.Shiyaku, 16, 33–37 (1993)), a fructosamine measuring method (refer to Clin. Chem. Acta. 127, 87–95 (1982)), a method of making colorimetric determination after oxidation with thiobarbituric acid (refer to Clin. Chem. Acta., 112, 179–204 (1981), radio immunoassay (RIA) and the like are known as methods of determining Amadori compounds.

However, each of the electrophoresis and the chromatography requires a long time for measurement with a complicated operation, while a measured absolute value of protein is so influenced by a substance having close affinity contained in a mixed substance that correct quantitative measurement is hard to make.

While RIA is superior in sensitivity, specificity and reproducibility, a labelling process is complicated and troublesome.

While the fructosamine measuring method utilizes reducing power of fructosamine in an alkaline solution, a measuring error is readily caused by an influence from another reducing substance.

While it is simple and effective if an Amadori compound such as saccharified protein can be determined by irradiating a substance with light and employing its light scattering spectrum, no such example of measuring an Amadori compound through such a light scattering spectrum has been reported.

SUMMARY OF THE INVENTION

Accordingly, an object of the present invention is to provide a method of quantitatively measuring an Amadori compound by a simple optical method utilizing light scattering.

The present invention is adapted to irradiate a sample containing an Amadori compound with excitation light of a single wavelength for receiving scattering light from the sample and separating the same into its spectral components for obtaining a light scattering spectrum, and make quantitative measurement of the Amadori compound through a light scattering peak existing at 820 to 840 $cm^{-1}$, 1655 to 1660 $cm^{-1}$, 2000 to 2020 $cm^{-1}$, 2080 to 2100 $cm^{-1}$, 2460 to 2470 $cm^{-1}$ or 2530 to 2600 $cm^{-1}$ in shift wavenumber with respect to the excitation wavelength in the light scattering spectrum.

In the light scattering spectrum obtained by irradiating the sample containing an Amadori compound with excitation light of a single wavelength, light scattering peaks overlap with a fluorescence spectrum. When an arithmetic operation of removing the fluorescence spectrum part is performed, it is easy to obtain a peak intensity or an integral value of any of the light scattering peaks. Then, quantitative measurement of the Amadori compound can be carried out on the basis of the peak intensity or the integral value thus obtained.

Thus, the present invention is simply adapted to irradiate a sample with excitation light of a single wavelength, receive scattered light from the sample and separate the same into its spectral components, whereby an Amadori compound can be quantitatively measured by a simple optical measuring method.

The quantitative measurement includes both of the case of measuring the amount of an Amadori compound contained in a sample, and the case of measuring the saccharification ratio of protein or the like in the sample. The saccharification ratio is defined as follows:

$$\frac{\text{(Amadori compound)}}{\text{(Amadori compound + protein or the like)}}$$

Every measured value can be obtained through a calibration curve.

In the obtained light scattering spectrum, the fluorescence spectrum reflects the total sum of (Amadori compound+ protein or the like). In a preferred method of measuring the saccharification ratio of protein or the like, therefore, correct measurement can be made by employing the ratio I/S of a peak intensity or an integral value I of any of light scattering peaks of the light scattering spectrum to an integral value S of a wavenumber region arbitrary set by excluding 820 to 840 $cm^{-1}$, 1655 to 1660 $cm^{-1}$, 2000 to 2020 $cm^{-1}$, 2080 to 2100 $cm^{-1}$, 2460 to 2470 $cm^{-1}$ and 2530 to 2600 $cm^{-1}$ in shift wavenumber with respect to the excitation wavelength in the light scattering spectrum.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1A:
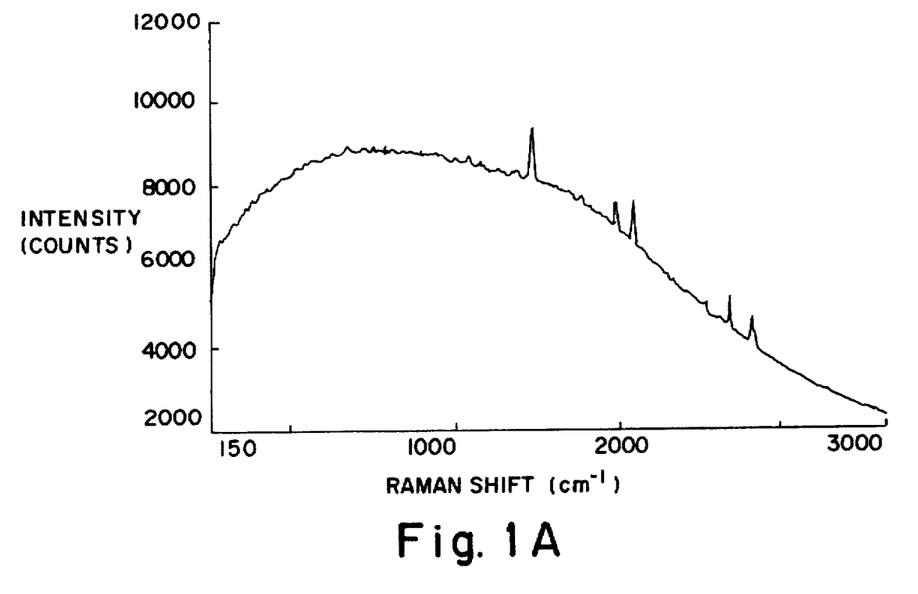
FIGS. 1A and 1B illustrate the light scattering spectra of human serum albumin samples having saccharification ratios of 24.1% and 58.2% respectively.
Figure 1B:
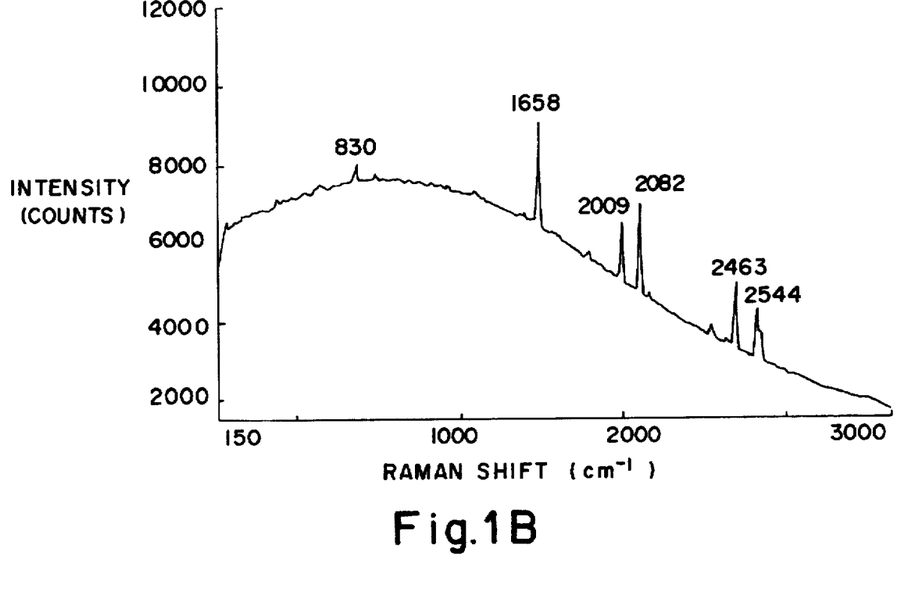

FIGS. 1A and 1B illustrate light scattering spectra obtained by irradiating human serum albumin aqueous solutions of 10 mg/dl in concentration having saccharification ratios of 24.1% and 58.2% respectively with laser beams of 632.8 nm in wavelength emitted from an He—Ne laser unit of 7 mW in output and exciting the same respectively. Referring to these figures, the axes of abscissas show light scattering shifts from the wavelengths of the He—Ne laser beams in wavenumbers, and the axes of ordinates show scattered light intensities.

Figure 2:
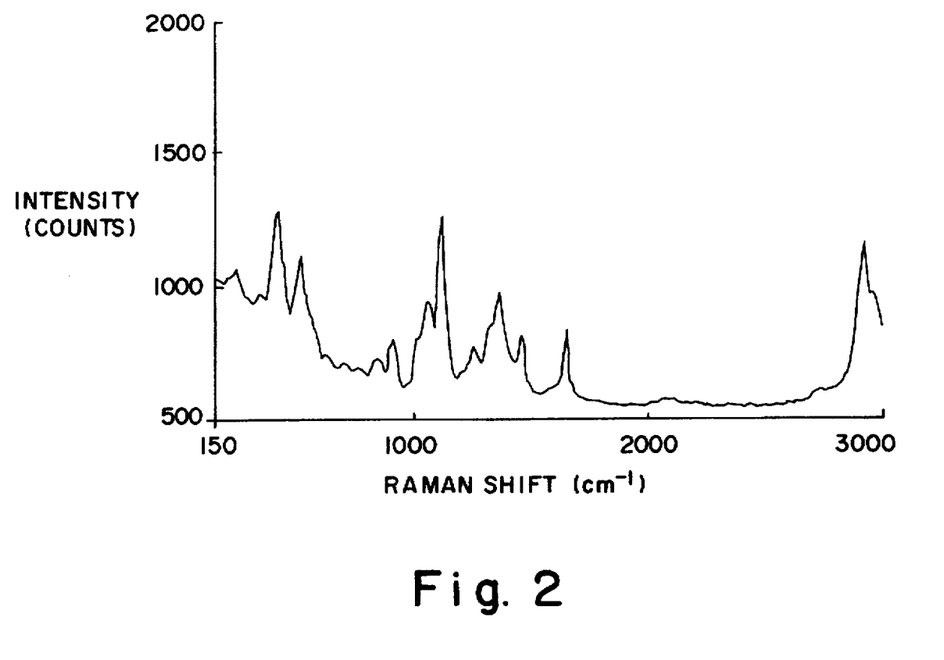
FIG. 2 illustrates the light scattering spectrum of an aqueous glucose solution of a high concentration.

In the light scattering spectra shown in FIGS. 1A and 1B, sharp peaks appear on the same light scattering shift positions, and the peak intensities are higher in the sample having the higher saccharification ratio. When light scattering spectra of glucose aqueous solutions having similar concentrations to the samples shown in FIGS. 1A and 1B were measured, no likes of peaks were observed. FIG. 2 shows the light scattering spectrum of a glucose aqueous solution having a high concentration of 10000 mg/dl, and some peaks appearing in this figure are different in position from the sharp peaks shown in FIGS. 1A and 1B. Consequently, it is understood that the sharp light scattering peaks appearing in FIGS. 1A and 1B are not by glucose but by saccharified albumin.

Referring to FIGS. 1A and 1B, angled, high and loose peaks are fluorescence from albumin and saccharified albumin, and the light scattering peaks by saccharified albumin overlap with and project from the high fluorescence peaks.

The light scattering peaks by saccharified albumin exist around 830 $cm^{-1}$, 1658 $cm^{-1}$, 2009 $cm^{-1}$, 2082 $cm^{-1}$, 2463 $cm^{-1}$ and 2544 $cm^{-1}$ in shift wavenumber from the wavelengths of the He—Ne laser beams.

Figure 3A:
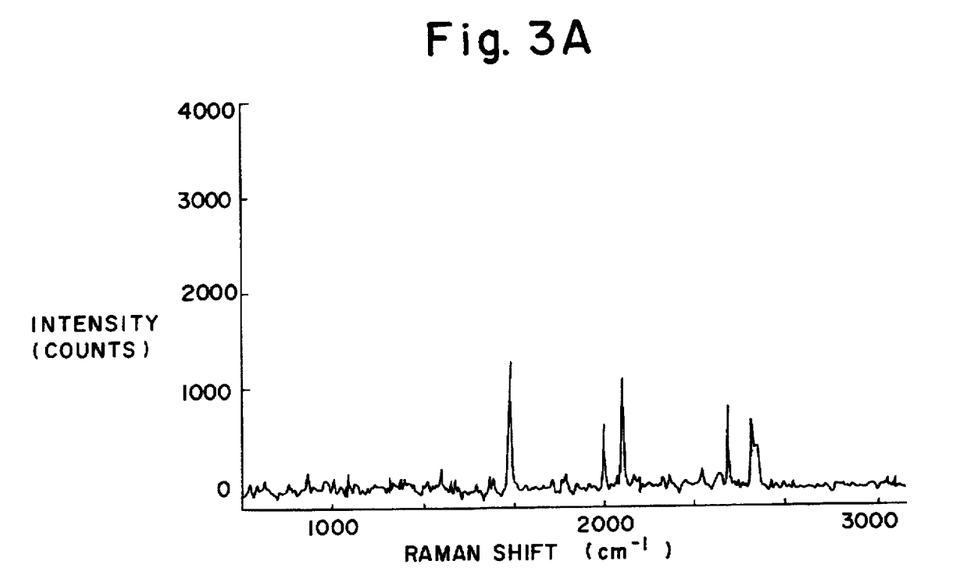
FIGS. 3A and 3B illustrate light scattering spectra obtained by performing an arithmetic operation of removing fluorescence spectra from the spectra shown in FIGS. 1A and 1B.
Figure 3B:
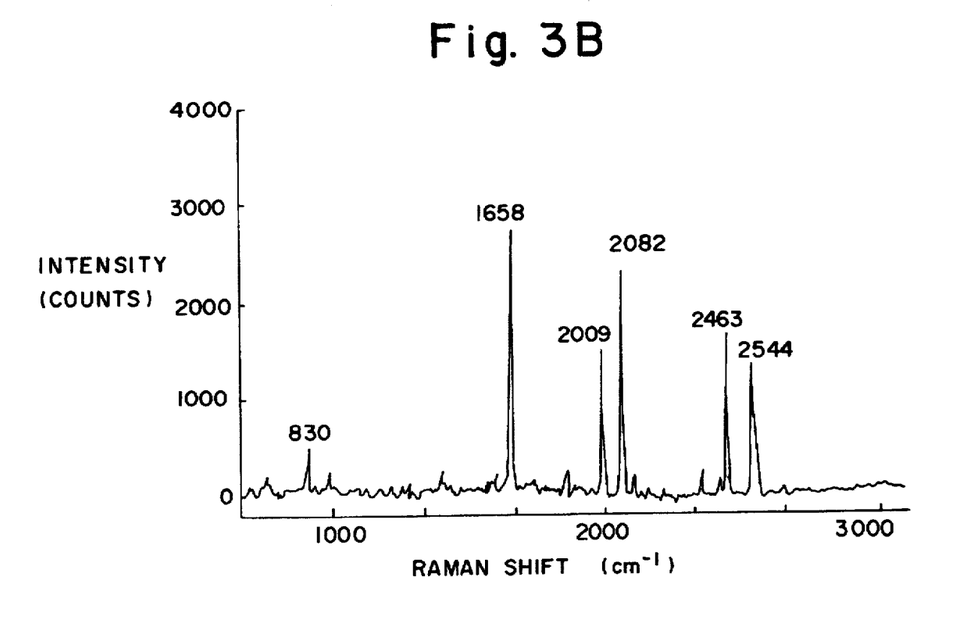

FIGS. 3A and 3B illustrate light scattering spectra obtained after removing the fluorescence spectrum parts from the light scattering spectra shown in FIGS. 1A and 1B as background signals respectively. Thus, the peak intensities and the peak integral values (areas) of the light scattering peaks can be readily obtained by removing the fluorescence spectrum parts.

Figure 4:
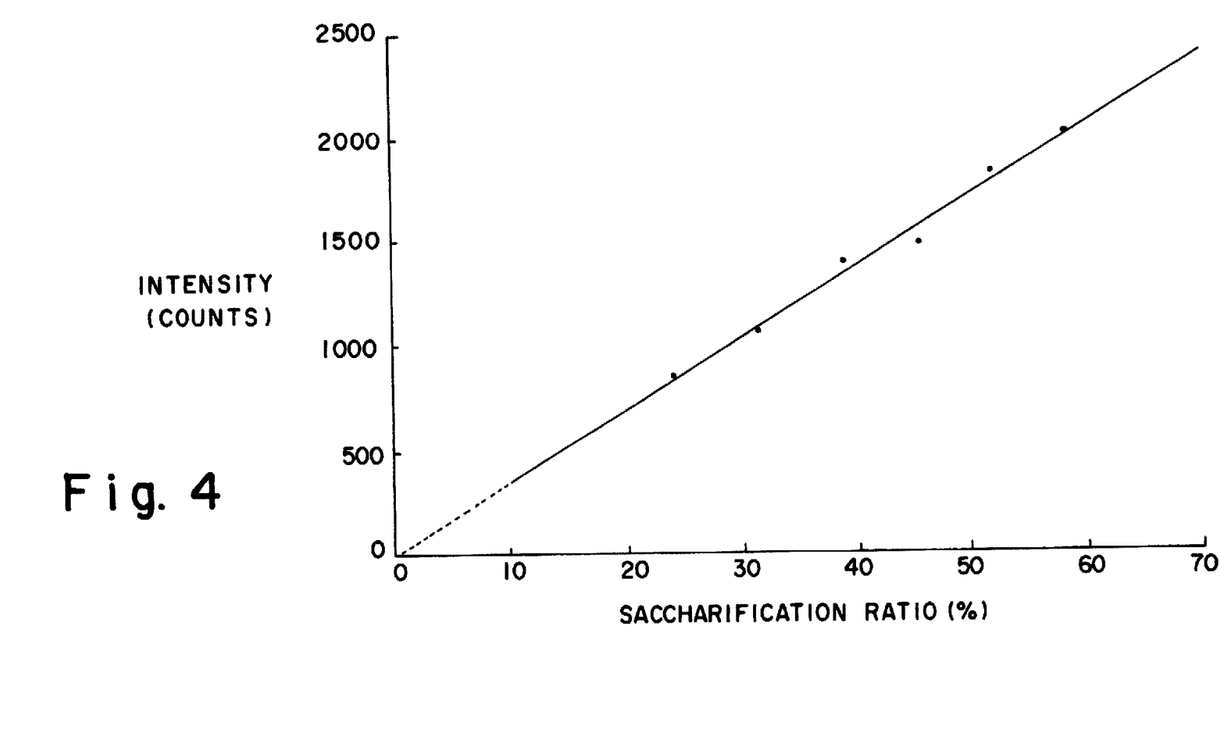
FIG. 4 illustrates a calibration curve showing the relation between peak intensities of single peaks of light scattering spectra and saccharification ratios.

FIG. 4 illustrates the relation between saccharification ratios and peak heights after removal of fluorescence spectrum parts as to standard samples of human serum albumin aqueous solutions having different saccharification ratios. A peak around 1658 $cm^{-1}$ in shift wavenumber from the wavelength of an He—Ne laser beam was measured. Standard samples of human serum albumin aqueous solutions having saccharification ratios of 24.1% and 58.2% are commercially available. Standard samples of other saccharification ratios were prepared by blending the commercially available standard samples with each other. The standard samples shown in FIG. 4 have saccharification ratios of 24.1%, 31.3%, 38.7%, 45.5%, 51.9% and 58.2% respectively. The numerical values of the saccharification ratios of these standard samples were measured with a fully automatic glycoalbumin fraction determination apparatus GAA-2000 (product by Kyoto Daiichi Kagaku Co., Ltd.).

According to FIG. 4, there is a linear relation between the saccharification ratios and the peak intensities of the light scattering peaks, and hence the results can be employed as a calibration curve for saccharification ratios. Further, (saccharified albumin+albumin) concentrations of the standard samples employed for measuring the data for the calibration curve are constant, and hence this calibration curve can also be diverted to that expressing saccharified albumin concentrations and peak intensities of light scattering peaks. When this calibration curve is employed, therefore, the saccharification ratio or the saccharified albumin concentration can be obtained as to an unknown sample by measuring a peak intensity of a light scattering spectrum.

Figure 5:
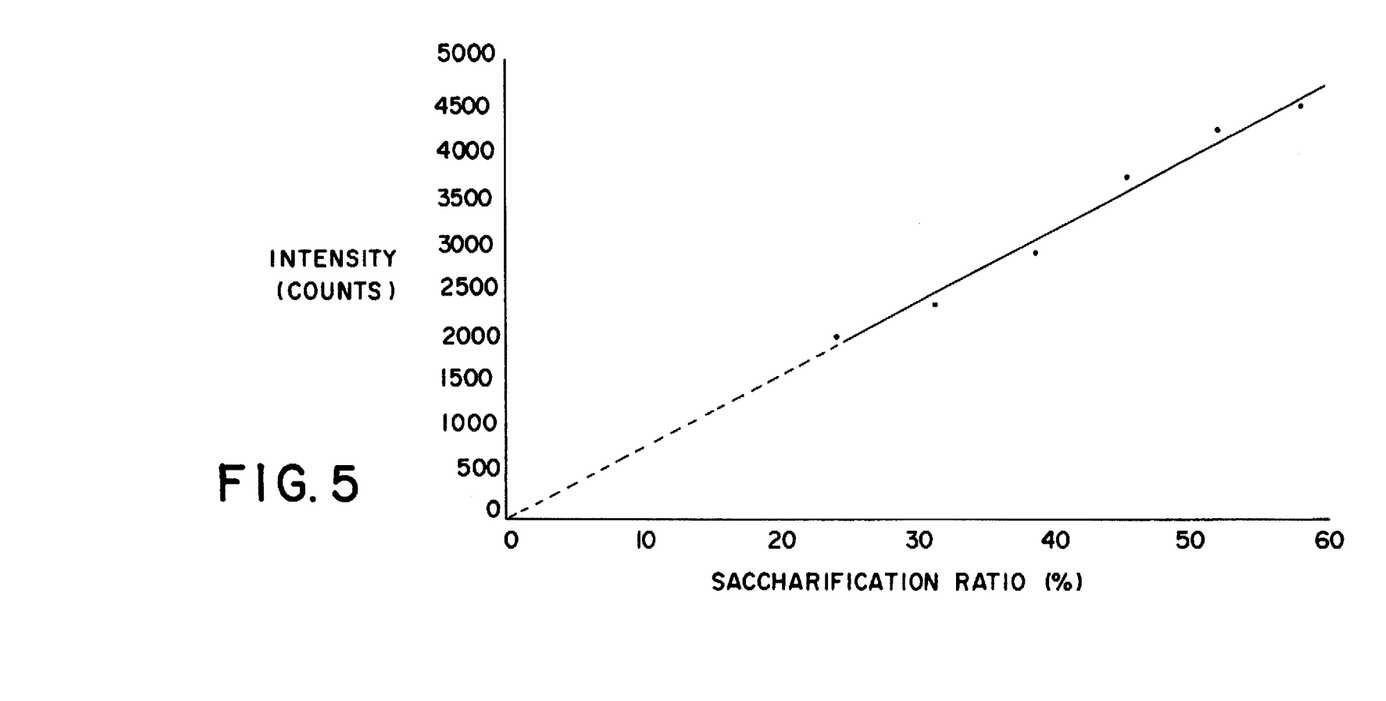
FIG. 5 illustrates a calibration curve showing the relation between integral values of the single peaks of the light scattering spectra and the saccharification ratios.

FIG. 5 illustrates results obtained by measuring the relation between the saccharification ratios and the light scattering peak integral values through the integral values of the same peaks of the light scattering spectra by the same standard samples. Also in this case, a linear relation is obtained between the saccharification ratios and the peak integral values, and this relation can also be utilized as a calibration curve. Therefore, the saccharification ratio or the saccharified albumin concentration can be obtained as to an unknown sample by measuring a peak integral value in place of the peak intensity of the peak of the light scattering spectrum.

The linear relations of FIGS. 4 and 5 similarly hold also as to the remaining light scattering peaks shown in FIGS. 3A and 3B.

Figure 6:
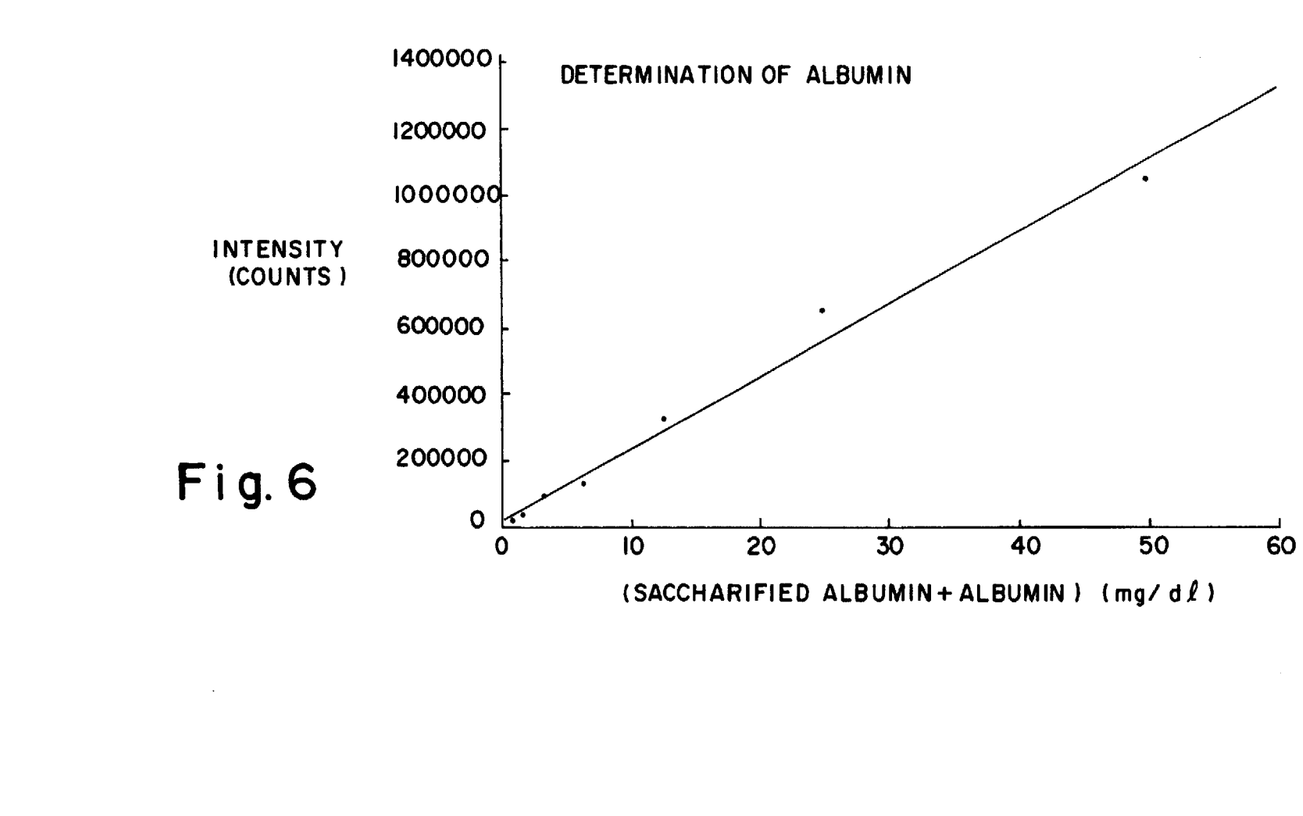
FIG. 6 illustrates the relation between albumin concentrations and integral values of fluorescence spectra.

In order to obtain the saccharification ratio of an unknown sample from the calibration curve showing the relation between the saccharification ratios and the peak intensities or the peak integral values shown in FIGS. 4 or 5, it is necessary to adjust the concentration of the unknown sample so that its (saccharified albumin+albumin) concentration is identical to those of the standard samples, or convert the measured value so that the (saccharified albumin+albumin) concentration is identical. In the light scattering spectra shown in FIGS. 1A and 1B, on the other hand, the fluorescence spectra are also detected at the same time in addition to the light scattering peaks. FIG. 6 illustrates results obtained by measuring integral values (intensities on the axis of ordinates) in a region of 416.508 to 1434.74 $cm^{-1}$ in shift wavenumber from the wavelength of the He—Ne laser beam in the fluorescence spectra as to standard samples having different (saccharified albumin+albumin) concentrations. A linear relation is obtained between the (saccharified albumin+albumin) concentrations and the integral values of the fluorescence spectra, and hence the saccharification ratios obtained from the peak intensities or the peak integral values of the light scattering peaks of saccharified albumin can be corrected by the (saccharified albumin+albumin) concentrations on the basis of the integral values of the fluorescence spectra. The wavenumber region for integrating the fluorescence spectra can be arbitrarily selected so far as the fluorescence spectra appear in the region, and is not restricted to the above.

When the ratio I/S of a peak intensity or an integral value I of any of the light scattering peaks to an integral value S of an arbitrarily set wavenumber region of a fluorescence spectrum part of a light scattering spectrum is employed as a parameter for obtaining a calibration curve showing the relation between saccharification ratios and I/S values as to a plurality of standard samples having different saccharification ratios, and I/S values of the light scattering peaks employed for forming the calibration curve are measured as to an unknown sample and applied to the calibration curve, a saccharification ratio corrected with the albumin concentration can be obtained.

While measurement is made as to saccharified albumin among saccharified protein in the above description, these light scattering peaks are observed in common for Amadori compounds such as saccharified peptide and saccharified amino acid, in addition to other saccharified protein. While those clinically important among Amadori compounds are saccharified albumin, saccharified hemoglobin and fructosamine which are saccharified protein, the present invention is also applicable to other Amadori compounds.

Figure 12A:
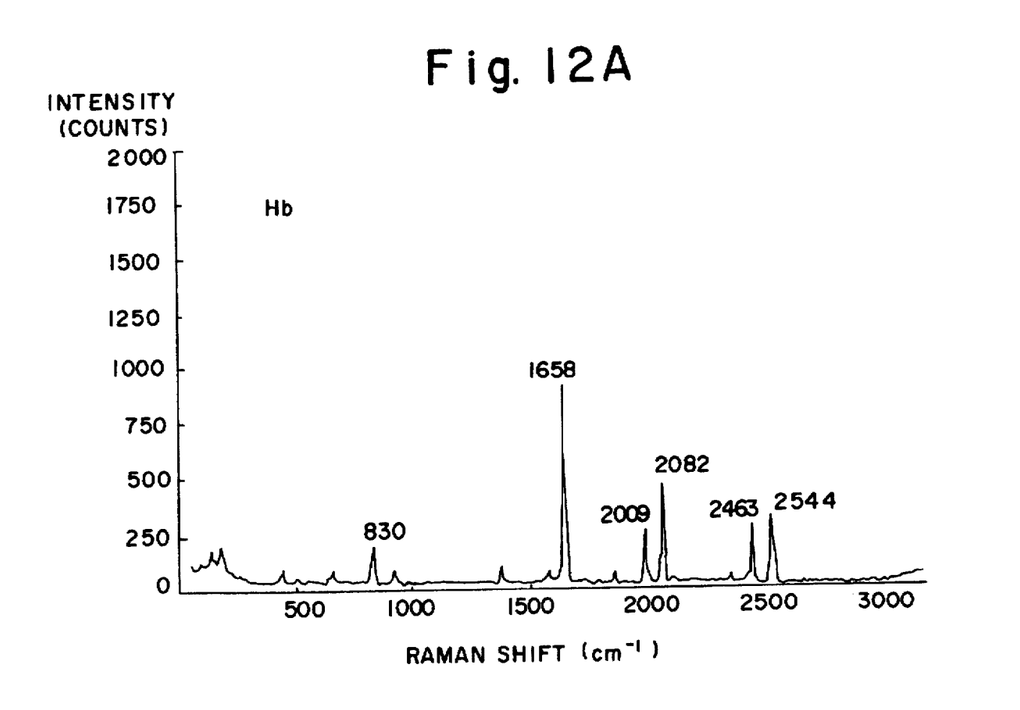
FIG. 12A illustrates a light scattering spectrum of human blood hemoglobin sample (unknown saccharification ratio) after removing fluorescence spectrum.

FIG. 12A illustrates a light scattering spectrum of human blood hemoglobin sample (unknown saccharification ratio) as another example of saccharified protein. The spectrum is obtained by irradiating the human blood hemoglobin aqueous solution with laser beam of 632.8 nm in wavelength emitted from an He—Ne laser unit of 7 mW in output and removing a fluorescence spectrum part as background signal. Also in the spectrum of FIG. 12A, sharp peaks appear on the same light scattering shift positions as in the spectra of FIGS. 3A and 3B.

Figure 12B:
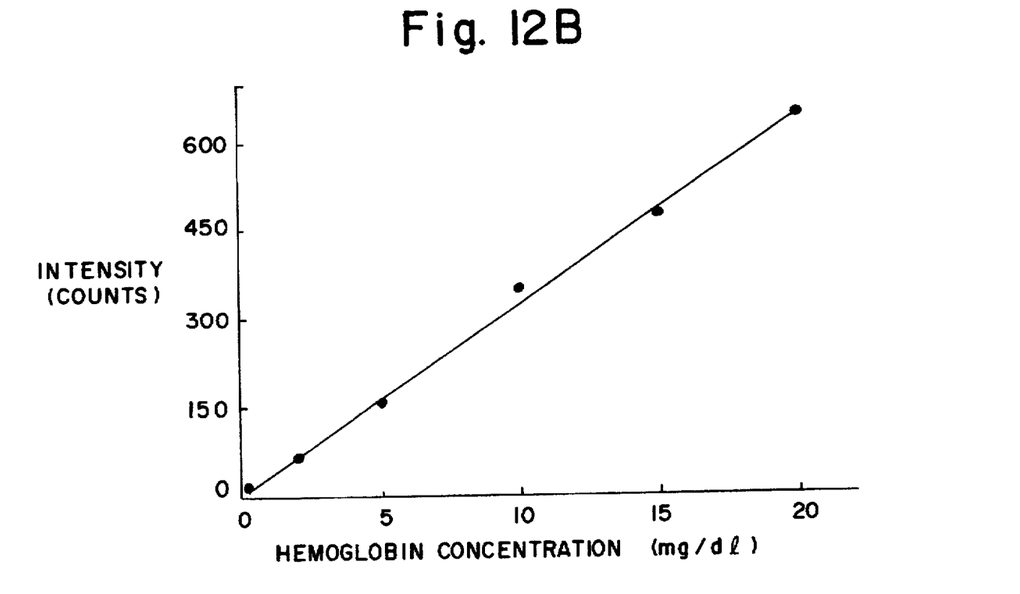
FIG. 12B illustrates a relation between hemoglobin concentrations and integral values of fluorescence spectra.

FIG. 12B illustrates a result obtained by measuring integral values (intensities on the axis of ordinate) in an adequate region in shift wavenumber from the wavelength of the He—Ne laser beam in the fluorescence spectrum as to standard samples having different hemoglobin concentrations. Also in the case of hemoglobin, a linear relation is obtained between the hemoglobin concentrations (i.e. saccharified hemoglobin+hemoglobin) and the integral values of the fluorescence spectra, and hence the saccharification ratios obtained from the peak intensities or the peak integral values of the light scattering peaks of saccharified hemoglobin can be corrected by the hemoglobin concentrations on the basis of the integral values of the fluorescence spectra.

Figure 7A:
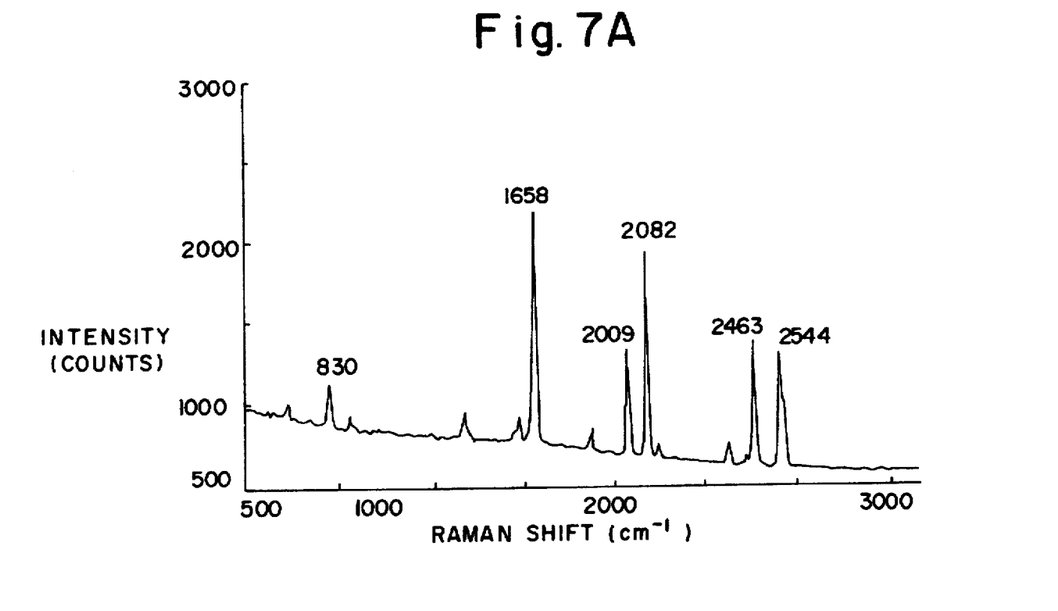
FIGS. 7A and 7B illustrate light scattering spectra of an Amadori compound before and after addition of a decomposition enzyme respectively.
Figure 7B:
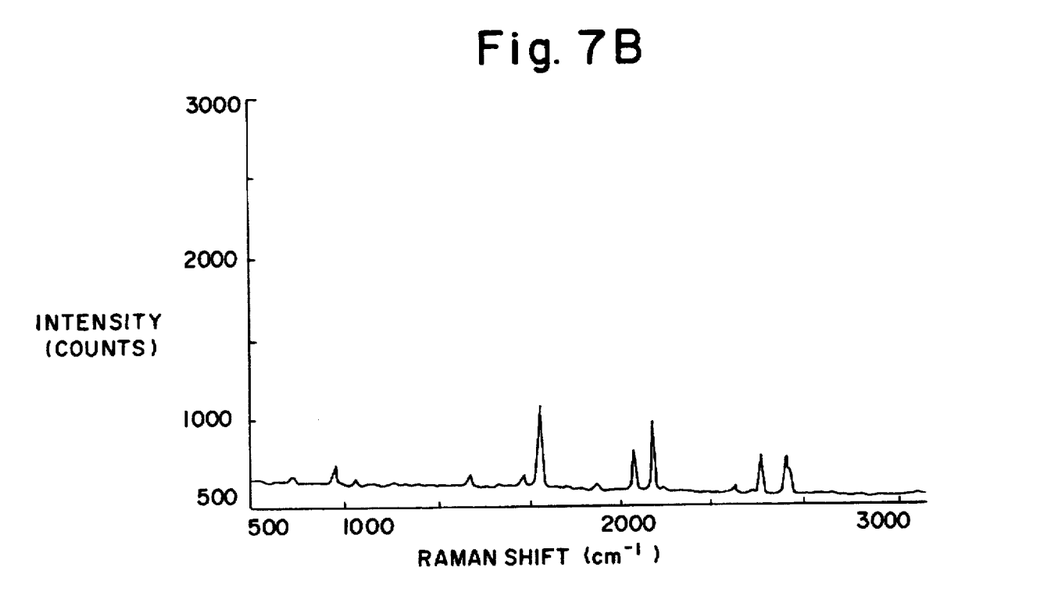
Figure 8:
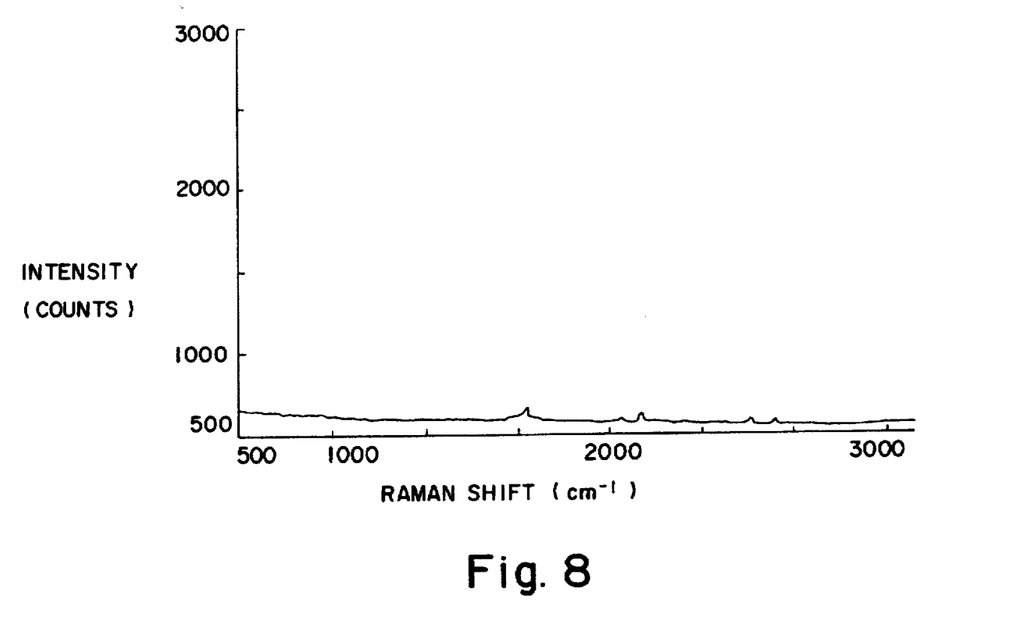
FIG. 8 illustrates the light scattering spectra of $N^\alpha$-Z-lysine.

FIGS. 7A and 7B illustrate results obtained by decomposing saccharified amino acid which is an Amadori compound with enzyme fructosylamino acid oxidase or the like specifically reacting with a bonded portion (fructose structure) between glucose and amino acid and investigating changes of peaks as an example showing that the six light scattering peaks in each of FIGS. 1A and 1B are those specific to an Amadori compound. FIG. 7A illustrates a light scattering spectrum by He—Ne laser excitation of an $N^{\epsilon}$-fructosyl-$N^{\alpha}$-Z-lysine (FZL) aqueous solution which is saccharified amino acid before reaction with such an enzyme. A light scattering spectrum obtained after reaction of the sample solution with the saccharified amino acid decomposition enzyme is shown in FIG. 7B, and peak intensities of the peaks specific to the Amadori compound are reduced as compared with the spectrum shown in FIG. 7A. A light scattering spectrum obtained by irradiating a standard sample of $N^{\alpha}$-Z-lysine ($\alpha$ZL) which is amino acid resulting from decomposition of FZL by the saccharified amino acid decomposition enzyme with an He—Ne laser beam is shown in FIG. 8, wherein no specific light scattering peaks appearing in FIGS. 7A and 7B are observed.

Figure 9:
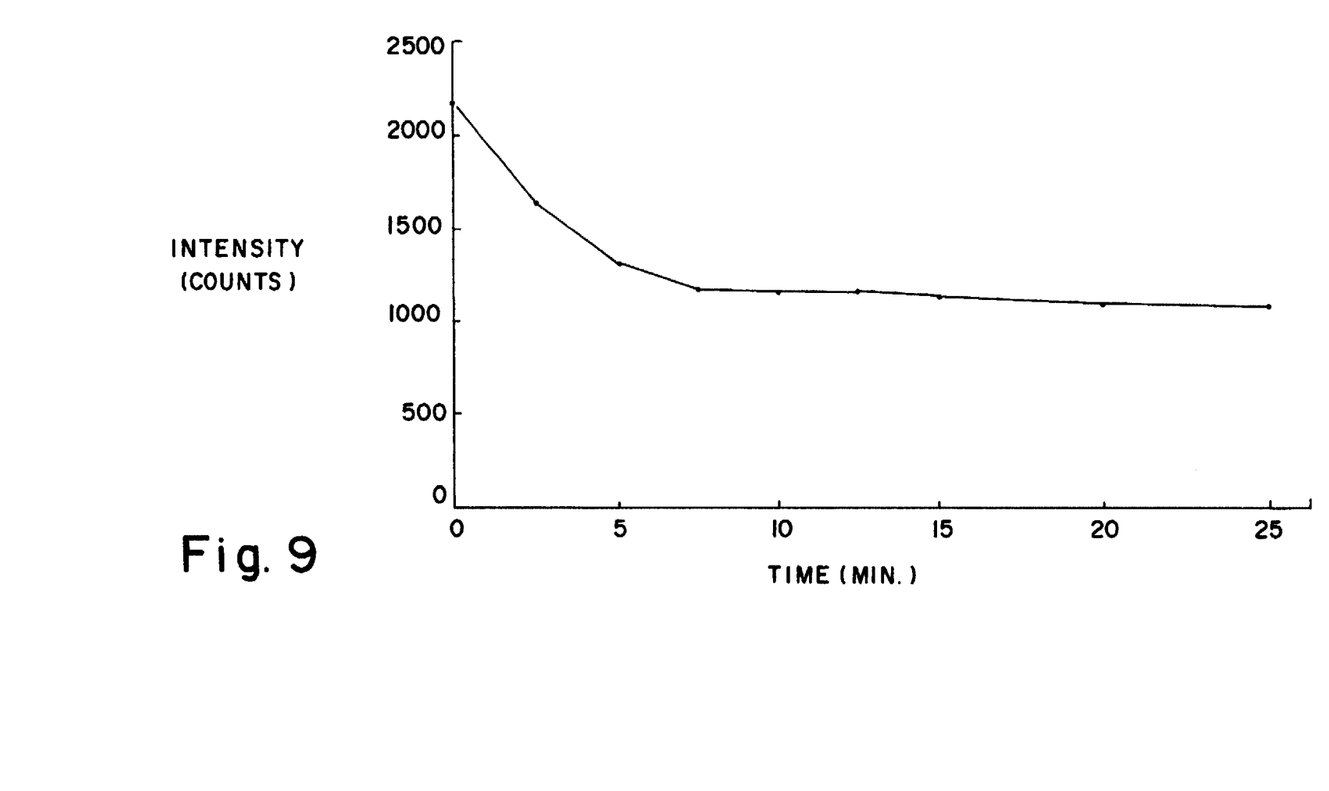
FIG. 9 illustrates changes of light scattering peaks with time from immediately after addition of the decomposition enzyme in the measurement shown in FIGS. 7A and 7B.

Results obtained by measuring changes of the peak intensities at the peaks of 1658 $cm^{-1}$ in shift wavenumber from the He—Ne laser wavelength with respect to times from addition of the saccharified amino acid decomposition enzyme in FIGS. 7A and 7B are shown in FIG. 9. The saccharified amino acid is decomposed by the decomposition enzyme and the peak intensities are reduced with time. Thus, it is understood that these characteristic light scattering peaks are those by bonding between sugar and amino acid.

Figure 13A:
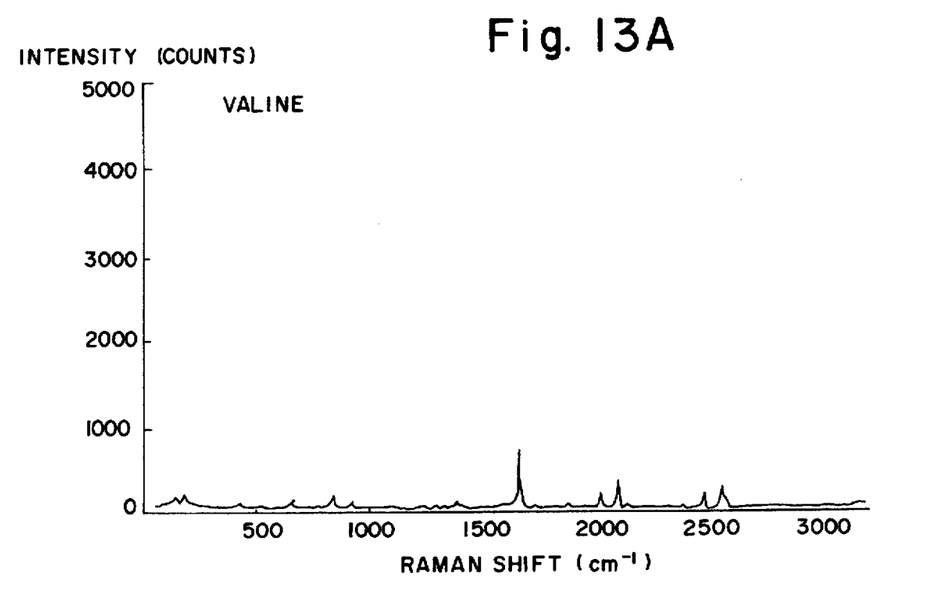
FIGS. 13A and 13B illustrate light scattering spectra of valine and saccharified valine respectively.
Figure 13B:
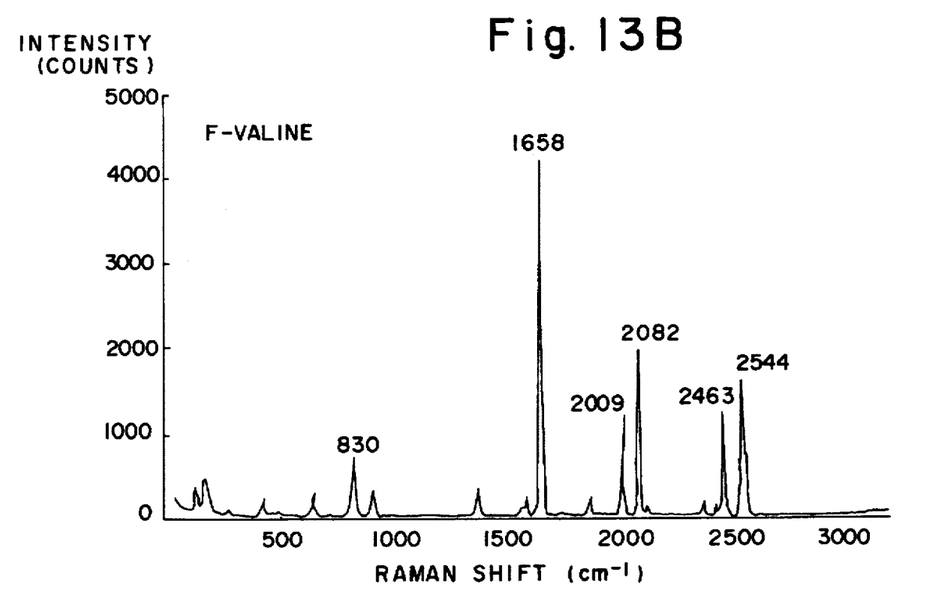

FIGS. 13A and 13B illustrate light scattering spectra of valine as another amino acid and saccharified valine as saccharified amino acid thereof respectively. The spectrum of saccharified valine also has characteristic light scattering peaks of Amadori compound.

Figure 10:
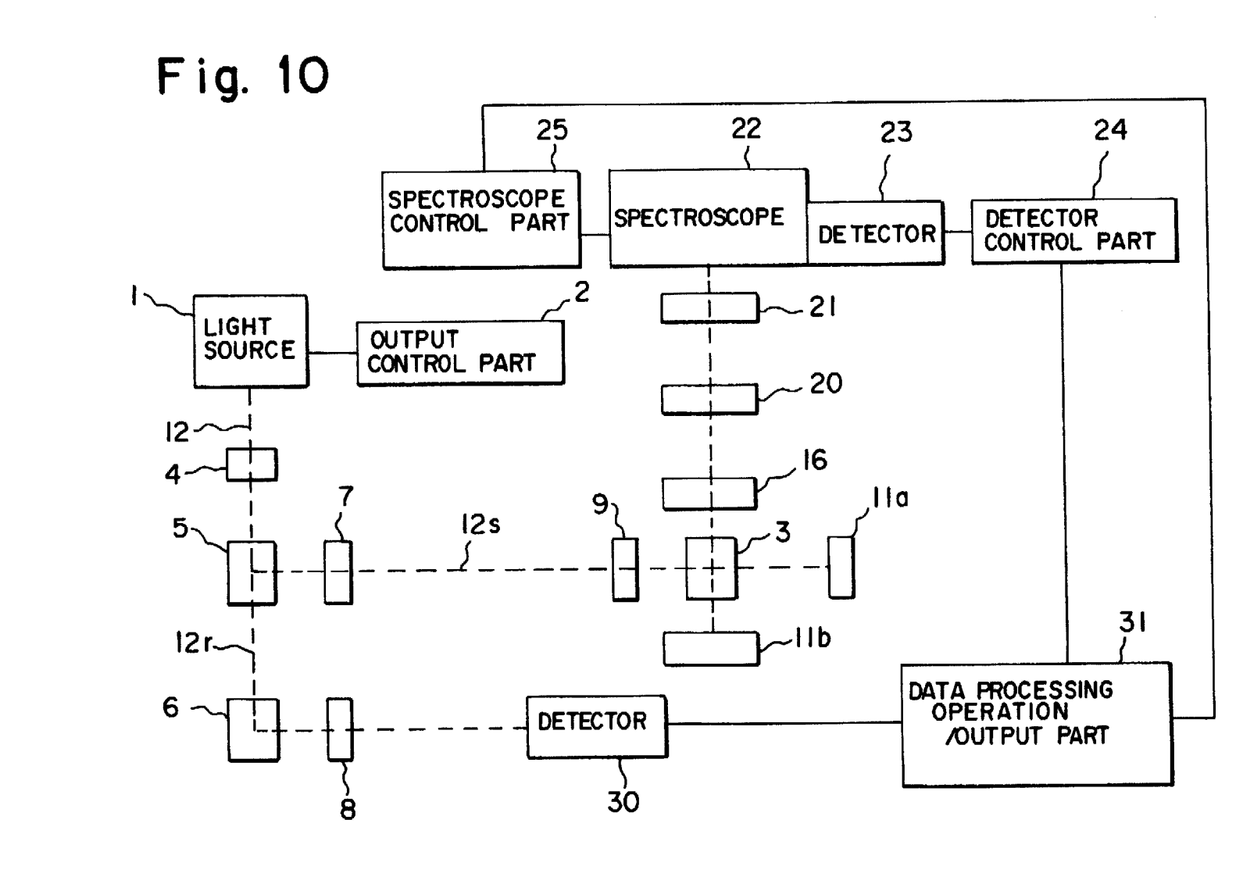
FIG. 10 is a block diagram showing an exemplary measuring apparatus for carrying out the present invention.

An exemplary apparatus for measuring a light scattering spectrum in accordance with the present invention is described with reference to FIG. 10. Numeral 1 denotes an excitation light source, which is prepared from a laser unit, for example. The laser unit can be selected from those of wide wavelength ranges over near ultraviolet to near infrared regions such as a continuously oscillating Ar ion laser unit, a Kr ion laser unit, an He—Ne laser unit, an He—Cd laser unit, an Nd:YAG laser unit and a pulse laser unit. Alternatively, a halogen lamp or the like can be employed as a light source other than a laser unit. It is assumed here that an He—Ne laser unit is employed as the light source 1. Numeral 2 denotes a power supply unit for controlling the output of the light source 1. Numeral 4 denotes a bandpass filter, which is adapted to cut a sideband from a laser beam 12 emitted from the light source 1. The laser beam 12 is separated by a half mirror 5 into an excitation beam 12s on a sample side and a reference beam 12r on a reference side, so that the excitation beam 12s is condensed on and introduced into a cell 3 by a lens 9 through a bandpass filter 7 for cutting wavelength light generated by the half mirror 5.

The cell 3, which is an angular-cylindrical scattered light cell of quartz, stores a sample solution and is kept at a constant temperature of 25° C., for example. A mirror 11a is arranged in the direction of incidence of the excitation beam 12s in order to reinforce scattered light generated from the reactive solution stored in the cell 3, so that the excitation beam 12s is transmitted through the cell 3, thereafter reflected by the mirror 11a and introduced into the cell 3 again thereby reinforcing light scattering. Another mirror 11b is arranged in a direction which is at an angle of 90° to the direction of incidence of the excitation beam 12s for reflecting light toward a spectroscope 22, so that the scattered light generated from the cell 3 is condensed by condenser lenses 16 and 20 along with the excitation beam 12s and Rayleigh scattered light with inclusion of that reflected by the mirror 11b, and condensed on the spectroscope 22 through a filter 21. The filter 21 is adapted to cut the components of the excitation beam 12s and the Rayleigh scattered light for introducing only scattered light wavelength-shifted from the excitation wavelength and a fluorescence component into the spectroscope 22. A detector 23 is formed by that of a multichannel detection system by a polychrometer in which a plurality of detecting elements are arranged along the direction of dispersion of the spectroscope 22. Numeral 24 denotes a detector control part for taking out an output from the multichannel detector 23 every wavelength.

The spectroscope 22 can be formed by a scan spectroscope, so that the detector 23 comprises a single detecting element. In this case, a spectroscope control part 25 is required for wavelength-scanning the spectroscope 22.

On the other hand, the reference beam 12r divided from the excitation beam 12s by the half mirror 5 is bent by a mirror 6 toward a detector 30 and introduced into the detector 30 through a bandpass filter 8 for cutting wavelength light generated in the mirror 6, so that the light source intensity is detected.

A data processing operation/output part 31 corrects a scattered light detected value by the spectroscope 22 and the detector 23 with a detected value of the detector 30 for the reference beam 12r indicating the light source intensity, and obtains a light scattering spectrum. When quantitative measurement is performed, the data processing operation/output part 31 holds calibration curve data formed by previous measurement, and calculates a saccharide concentration or a saccharification ratio from a peak intensity or a peak area obtained by measuring an unknown sample, or a value obtained by correcting the same with an area value of a fluorescence spectrum on the basis of the calibration curve. When the spectroscope 22 performs wavelength scanning, the data processing operation/output part 31 performs wavelength scanning through the spectroscope control part 25.

Figure 11A:
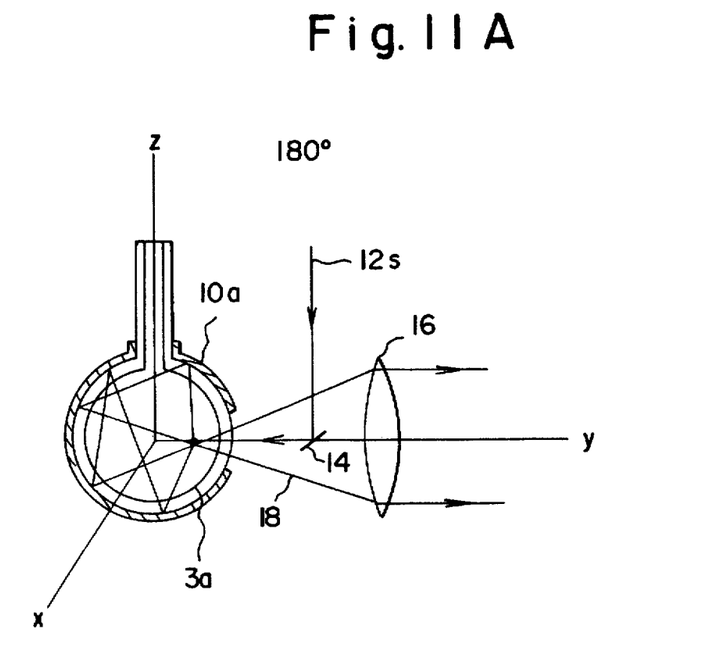
FIGS. 11A and 11B are sectional views showing exemplary cell parts in the measuring apparatus for taking out 180° reinforced scattering and 90° reinforced scattering respectively.
Figure 11B:
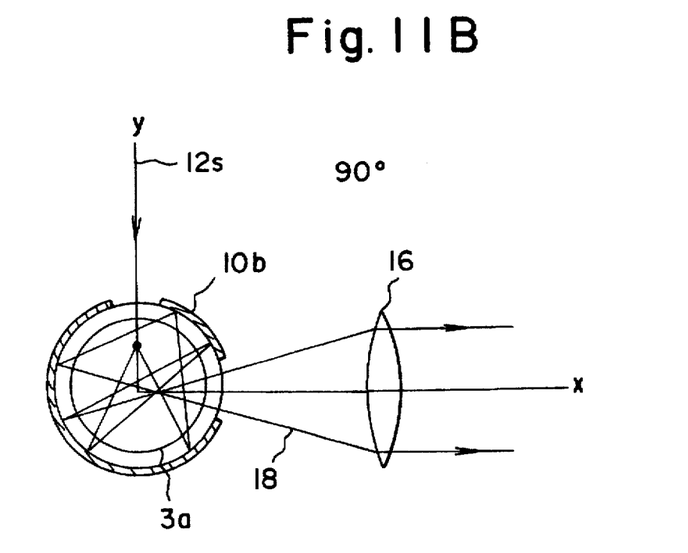

FIGS. 11A and 11B illustrate exemplary cells for further effectively reinforcing light scattering by excitation light.

Referring to FIG. 11A, a cell 3a is in the form of a round-bottomed flask which is made of a transparent material such as quartz or polyethylene terephthalate, and stores a sample solution. This cell 3a is engaged in a cell holder 10a which is in the form of an integrating sphere. The cell holder 10a has a reflecting surface on its inner surface, and is provided with a window for receiving an excitation beam 12s and taking out scattered light in a direction which is at 180° to the direction of incidence. The excitation beam 12s is bent by a mirror 14 and introduced into the cell 3a through the window of the cell holder 10a. Numeral 16 denotes a condenser lens for condensing scattered light outgoing from the window of the cell holder 10a along with the excitation beam 12s. The excitation beam 12s which is applied to the sample solution stored in the cell 3a is repeatedly reflected by the inner surface of the cell holder 10a and taken out from the window of the cell holder 10a with light scattering, to be guided toward a spectroscope.

FIG. 11B shows a cell holder 10b which is provided with windows for taking out scattered light in a direction at 90° with respect to the direction of incidence of an excitation beam 12s. A cell 3a is engaged in the cell holder 10b which is in the form of an integrating sphere having a reflecting surface on its inner surface. The cell holder 10b is provided with a window for receiving the excitation beam 12s from a direction y and another window for taking out scattered light 18 in a direction x which is at 90° to the direction of incidence.

Although the present invention has been described and illustrated in detail, it is clearly understood that the same is by way of illustration and example only and is not to be taken by way of limitation, the spirit and scope of the present invention being limited only by the terms of the appended claims.

We claim:

1. A method of measuring an Amadori compound by irradiating a sample containing said Amadori compound with excitation light of a single wavelength, receiving scattered light from said sample and separating said scattered light into its spectral components for obtaining a light scattering spectrum, and performing quantitative measurement of said Amadori compound through a light scattering peak existing at 820 to 840 $cm^{-1}$, 1655 to 1660 $cm^{-1}$, 2000 to 2020 $cm^{-1}$, 2080 to 2100 $cm^{-1}$, 2460 to 2470 $cm^{-1}$ or 2530 to 2600 $cm^{-1}$ in shift wavenumber with respect to said excitation wavelength in said light scattering spectrum.

2. The method of measuring an Amadori compound in accordance with claim 1, wherein an arithmetic operation of removing a fluorescence spectrum part from said light scattering spectrum is performed and thereafter said quantitative measurement of said Amadori compound is performed on the basis of a peak intensity or an integral value of any said light scattering peak.

3. The method of measuring an Amadori compound in accordance with claim 1, wherein a concentration or a saccharification ratio of said Amadori compound being obtained on the basis of a peak intensity or an integral value of any said light scattering peak is corrected by an integral value of an arbitrarily set wavenumber region in said light scattering spectrum.

4. The method of measuring an Amadori compound in accordance with claim 1, wherein said measured Amadori compound is any one of saccharified albumin, saccharified hemoglobin and fructosamine.

5. The method of measuring an Amadori compound in accordance with claim 1, wherein an He—Ne laser unit is employed as an excitation light source.

6. The method of measuring an Amadori compound in accordance with claim 1, wherein saccharification ratio measurement of said Amadori compound is performed on the basis of the ratio I/S of a peak intensity or an integral value I of any said light scattering peak to an integral value S of a fluorescence spectrum of an arbitrarily set wavenumber region in said light scattering spectrum.

7. The method of measuring an Amadori compound in accordance with claim 6, wherein said integral value S of said fluorescence spectrum is that in an arbitrarily set wavenumber region excluding 820 to 840 $cm^{-1}$, 1655 to 1660 $cm^{-1}$, 2000 to 2020 $cm^{-1}$, 2080 to 2100 $cm^{-1}$, 2460 to 2470 $cm^{-1}$ and 2530 to 2600 $cm^{-1}$ in shift wavenumber with respect to said excitation wavelength in said light scattering spectrum.

* * * * *